(12) United States Patent  (10) Patent No.: US 8,449,658 B2
McAdams et al.  (45) Date of Patent: May 28, 2013

(54) HIGH-PRESSURE CAPILLARY DEGAS ASSEMBLY

(75) Inventors: Michael McAdams, Los Gatos, CA (US); Milton Liu, San Mateo, CA (US); Gary L. Gleave, Pleasanton, CA (US)

(73) Assignee: Dionex Corporation, Sunnyvale, CA (US)

( * ) Notice: Subject to any disclaimer, the term of this patent is extended or adjusted under 35 U.S.C. 154(b) by 290 days.

(21) Appl. No.: 13/027,148

(22) Filed: Feb. 14, 2011

(65) Prior Publication Data

US 2012/0204726 A1    Aug. 16, 2012

(51) Int. Cl.
*B01D 53/22*  (2006.01)
*B01D 19/00*  (2006.01)

(52) U.S. Cl.
USPC ............. 96/6; 96/8; 96/10; 95/46; 210/198.2

(58) Field of Classification Search
USPC ........ 96/4, 6, 8, 10, 11, 182, 193, 194; 95/46; 210/198.2
See application file for complete search history.

(56) References Cited

U.S. PATENT DOCUMENTS

| | | |
|---|---|---|
| 3,897,213 A | 7/1975 | Stevens et al. |
| 3,920,397 A | 11/1975 | Small et al. |
| 3,925,019 A | 12/1975 | Hamish et al. |
| 3,926,559 A | 12/1975 | Stevens |
| 4,265,634 A | 5/1981 | Pohl |
| 5,045,204 A | 9/1991 | Dasgupta et al. |
| 5,053,060 A * | 10/1991 | Kopf-Sill et al. .................. 95/46 |
| 5,352,360 A | 10/1994 | Stillian et al. |
| 5,569,365 A | 10/1996 | Rabin et al. |
| 5,980,742 A * | 11/1999 | Saitoh ......................... 210/198.2 |
| 6,225,129 B1 | 5/2001 | Liu et al. |
| 6,350,297 B1 | 2/2002 | Doyle et al. |
| 6,682,701 B1 | 1/2004 | Liu et al. |
| 6,942,718 B1 * | 9/2005 | Schmidt ............................. 96/6 |
| 6,955,922 B1 | 10/2005 | Liu et al. |
| 7,291,204 B2 * | 11/2007 | Suzuki et al. ..................... 95/46 |
| 7,390,386 B2 | 6/2008 | Srinivasan et al. |
| 7,635,428 B2 * | 12/2009 | Marui et al. ........................ 96/6 |
| 2003/0127392 A1 | 7/2003 | Srinivasan et al. |
| 2006/0037911 A1 * | 2/2006 | Dasgupta et al. .......... 210/198.2 |
| 2007/0095204 A1 * | 5/2007 | Gerner et al. ..................... 95/46 |
| 2008/0085216 A1 * | 4/2008 | Akechi et al. ...................... 96/6 |
| 2011/0036240 A1 * | 2/2011 | Taylor et al. ........................ 96/6 |
| 2011/0290726 A1 * | 12/2011 | Liu et al. ....................... 210/640 |
| 2012/0160096 A1 * | 6/2012 | Gottlieb et al. .................... 95/46 |

* cited by examiner

*Primary Examiner* — Jason M Greene
(74) *Attorney, Agent, or Firm* — Victor Johnson (57) ABSTRACT

A high-pressure capillary degas assembly includes an assembly block having an eluent inlet and an eluent outlet, and a separator support extending therebetween, a wash inlet and a wash outlet and a groove extending therebetween, a tubular separator extending within the assembly block, the separator having an inner surface and an outer surface, the inner surface defining an eluent fluid line fluidly interconnecting the eluent inlet and outlet, the outer surface abutting against the separator support and enclosing the groove to define a wash line within the groove. The separator may be configured to retain liquid in the eluent fluid line at a first pressure and allow gas to flow through the separator to the wash fluid line at a second pressure lower than the first pressure. A method of using the high-pressure capillary degas assembly is also disclosed.

21 Claims, 8 Drawing Sheets

HIGH-PRESSURE CAPILLARY DEGAS ASSEMBLY

BACKGROUND OF THE INVENTION

1. Field of the Invention

This invention relates, in general, to degas assemblies and more particularly to high-pressure capillary degas assemblies and methods for their use.

2. Description of Related Art

Ion chromatography is a common technique for analysis of sample materials. Conventional ion chromatography typically includes a chromatographic separation stage using an eluent containing an electrolyte and an eluent suppression stage followed by detection. In the chromatographic separation stage, analyte ions of interest in an injected sample are eluted through a separation column using an electrolyte as the eluent. In the suppression stage, electrical conductivity of the electrolyte is suppressed while not affecting the separated ions so that the ions may be determined by a conductivity cell. Such techniques are described in detail in U.S. Pat. Nos. 3,897,213, 3,920,397, 3,925,019 and 3,926,559.

Dilute solutions of acids, bases, or salts are commonly used as chromatographic eluents. Traditionally, these eluents are prepared off-line by dilution with reagent-grade chemicals. Off-line preparation of chromatographic eluents can be tedious and prone to operator errors, and often introduces contaminants. In recent years, several approaches that utilize the electrolysis of water and charge-selective electromigration of ions through ion-exchange media have been investigated by researchers to purify or generate high-purity ion chromatographic eluents. U.S. Pat. Nos. 6,225,129, 6,682,701, and 6,955,922 describe electrolytic devices that can be used to generate high purity acid and base solutions by using water as the carrier. Using these devices, high purity, contaminant-free acid or base solutions are automatically generated on-line for use as eluents in chromatographic separations. These devices simplify gradient separations that can now be performed using electrical current gradients, with minimal delay, instead of using a conventional mechanical gradient pump.

With conventional electrolytic eluent generators, however, gases can be introduced into the eluent during the electrolytic reaction or at other stages in the analysis process. For example, in a large capacity potassium hydroxide (KOH) generator, electrolysis reactions produce hydrogen and oxygen gases. When used in a chromatography system, the hydrogen gas, along with the KOH solution, is carried forward into the chromatographic flow path. If hydrogen gas is produced in a significant volume relative to the liquid flow, its presence can be detrimental to the detection process and other downstream chromatography processes.

One solution to the problem of a presence of gas in the eluent is disclosed by the above-mentioned U.S. Pat. No. 6,225,129 to Liu et al. The Liu '129 patent discloses a method for addressing the potential problem of hydrogen gas by application of Boyle's law. A flow restrictor is placed after the detector flow cell to create backpressure and elevate the pressure of the entire chromatography system. Under elevated pressure (e.g., 1000 psi), hydrogen gas is compressed to an insignificant volume compared to the eluent flow so that it does not interfere with the downstream chromatography process. But this approach has several drawbacks. Because of the elevated pressures, the detector flow cell must be capable of withstanding a pressure of at least 1000 psi. In the case of ion chromatography system using suppressed conductivity detection, the suppressor must also be capable of withstanding an elevated high-pressure. Therefore, this approach limits the type of components that can be used in an ion chromatography system employing an electrolytic eluent generator.

Another approach involves using an on-line gas removal device to remove hydrogen gas from the KOH solution. One way to remove the gas from an effluent is to pass the effluent through a gas removal device having a gas diffusion membrane prior to reaching the detection cell. An exemplar of a gas removal device used with a chromatography system is disclosed in U.S. Pat. No. 5,045,204 to Dasgupta et al.

The Dasgupta '204 patent discloses a system including a device for removal of gas (e.g., hydrogen) generated in the electrolytic cell from the product stream (e.g., sodium hydroxide). In one embodiment, the gas removal device is a gas diffusion cell including a plurality of blocks and a gas diffusion membrane separating a degassed product channel from a gas carrier channel. In another embodiment, gas-containing product is directed into a porous hydrophobic tube that is configured for the product to flow downwardly and then upwardly out of an exit port. The tube is formed of hydrophobic materials (e.g., as porous polytetraofluoroethylene (PTFE), (expanded)PTFE, Accurel®, or Celgard®) similar to the membrane. The hydrogen gas flows outwardly through the tube to a gas vent. As the KOH eluent stream passes through the tube under pressure, hydrogen gas diffuses through the tube and is carried to waste. In this manner gas is effectively removed from the eluent before it reaches the sample injector of the chromatography system so that the downstream chromatographic process is not affected. One advantage of this system is that a conventional detector flow cell and ion chromatography suppressor can be used.

The Liu '129 patent discloses a similar gas removal device for on-line removal of gas from the eluent solution. The gas removal device includes a gas-permeable tubing coaxially aligned within a protective tubing. The gas-permeable tubing functions like a membrane. In operation, the KOH solution containing hydrogen gas is pumped through the gas permeable tubing and the hydrogen gas escapes through the tubing. A stream of aqueous solution flowing in an annular space between the outside of the gas permeable tubing and the protective tubing carries away the released gas.

One problem with such conventional gas removal devices is that current gas diffusion materials cannot withstand pressures found in modern systems. Ion chromatography systems, in particular high-performance liquid chromatography (HPLC) systems, experience high in-line pressures. Conventional membrane materials have low burst pressures by comparison. By example, typical systems can rise above 1000 psi, and modern pumps can generate pressures in excess of 3000 psi and even 5000 psi. Such pressure levels are above the burst pressure of porous and gas-permeable tubing used for conventional gas removal devices such as those of the Dasgupta '204 and Liu '129 patents. Further, the low-pressure threshold of such conventional devices limits the capabilities of the overall system. For example, systems making use of such gas removal devices are limited to about 3000 psi in the separation column. High-pressure is desirable for greater efficiency and performance.

One solution to this has been to position the electrolytic eluent generator and the gas removal device on the low-pressure side of the system, meaning in the pump intake line, or external (off-line) to the system. However, these positioning solutions limit the effectiveness of the devices and add to the volume of the electrolytic eluent generation system, thus compromising the overall performance of the ion chromatography system.

Thus, there is need to develop a degasser device that can be used in conjunction with an electrolytic eluent generator in ion chromatography and liquid chromatography systems over a wider range of operational pressures. There is a continuing need for chromatography systems with increased efficiency and performance.

In light of the foregoing, it would be beneficial to have methods and apparatuses which overcome the above and other disadvantages of known gas removal devices and chromatography systems.

BRIEF SUMMARY OF THE INVENTION

One aspect of the present invention is directed to a high-pressure capillary degas assembly including an assembly block having an eluent inlet and an eluent outlet, and a separator support extending therebetween, a wash inlet and a wash outlet and a groove extending therebetween, a tubular separator extending within the assembly block, the separator having an inner surface and an outer surface, the inner surface defining an eluent fluid line fluidly interconnecting the eluent inlet and outlet, the outer surface abutting against the separator support and enclosing the groove to define a wash line within the groove. The separator may be configured to retain liquid in the eluent fluid line at a first pressure and allow gas to flow through the separator to the wash fluid line at a second pressure lower than the first pressure.

The assembly block may include a plurality of grooves extending between the wash inlet and the wash outlet, wherein outer surface of the separator encloses each of the plurality of grooves. The plurality of grooves may extend radially away from the separator. The plurality of grooves may extend along substantially the entire length of the separator. The plurality of grooves may collectively form the wash line which extends coaxially around the eluent line.

The assembly block may include a cut at least partially encircling the tubular separator fluidly coupled with one of the wash inlet and wash outlet. The annular cut may interconnect the plurality of grooves. The cut may be an annular cut encircling the tubular separator.

One or more of plurality of grooves may helically spiral about the tubular separator. Two or more of the plurality of grooves may intersect one another fluidly coupling the two or more grooves with one another.

The assembly block may include upper and lower plates, and respective upper and lower supports on the upper and lower plates. The upper and lower plates may have corresponding seal channels extending parallel to the separator support. The corresponding seal channels may receive a seal therein to fluidly seal the wash line. The upper and lower plates may have corresponding mating surfaces. At least one of said plurality of grooves may extend away from the separator and parallel to the mating surfaces. The upper and lower supports may have an inner diameter that is substantially equal to an outer diameter the outer surface of the separator. The inner diameter of the upper and lower supports may be less than the outer diameter of the separator thereby providing an interference fit between the separator and separator support.

The tubular separator may have a circular cross-section. The tubular separator may include inert polymer tubing. The polymer tubing may be amorphous fluoropolymer tubing. The polymer tubing may be polyetheretherketone (PEEK) tubing.

The eluent line may receive eluent from an eluent generator at a pressure up to at least approximately 3000 psi.

The methods and apparatuses of the present invention have other features and advantages which will be apparent from or are set forth in more detail in the accompanying drawings, which are incorporated herein, and the following Detailed Description of the Invention, which together serve to explain certain principles of the present invention.

BRIEF DESCRIPTION OF THE DRAWINGS

FIG. 7 is an enlarged cross-sectional view of the gas removal assembly taken along line 7-7 of FIG. 2.

FIG. 8A is an enlarged cross-sectional view of the gas removal assembly shown in FIG. 7, while FIGS. 8B and 8C are enlarged cross-sectional views of alternative groove configurations therefore.

DETAILED DESCRIPTION OF THE INVENTION

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Various aspects of the present invention are similar to the devices and systems described in U.S. Pat. Nos. 7,390,386, 6,682,701, 6,225,129, 5,569,365 and 5,045,204, and in U.S. Patent Application No. 2003/0127392, the entire contents of which are incorporated herein for all purposes by this reference. In addition, certain aspects of the present invention are similar to the assemblies and systems described in copending U.S. patent application Ser. No. 12/791,732, the entire contents of which is also incorporated herein for all purposes by this reference.

The gas removal assembly and method of the present invention will first be broadly described in combination with an ion chromatographic system. The gas removal device and method of the present invention, however, are also applicable to liquid chromatography forms other than ion chromatography. The present inventions are also applicable to other gas removal and separation applications including, but not limited to, industrial applications involving gassified fluid streams. An example of use of a conventional gas separation device for gas clean-up and purification of a liquid stream is disclosed by U.S. Pat. No. 6,350,297, the entire contents of which are incorporated herein for all purposes by this reference.

By "gassified" it is meant that the liquid stream includes a gas component, whether resulting from a prior process or occurring naturally. "Degassed" refers to the resulting product after removal of the gas in accordance with the invention. "Degassed", "degas", and "degasser" are used interchangeably in various respects to refer to the device and resulting product using the device.

"High-pressure" and "low-pressure" are to be understood as used in the analytical, chemical, and mechanical arts and are generally relative used with reference to each other under operational conditions. "High-pressure" generally refers to an elevated pressure or pressurized. "Low-pressure" generally refers to an unaltered local pressure or pressure below the "high-pressure." In various respects, "low-pressure" refers to a decreased pressure level obtained by a process or device of the invention.

"Wash fluid" refers generally to a fluid or other means for washing or evacuating the removed gas species from the channel. In various respects, "wash fluid" refers to a gas or void such as a vacuum. "Liquid" and "aqueous" are used essentially interchangeably. In various aspects, the wash fluid is essentially 100% organic solvents. In various aspects, the wash fluid is a mixture of water and organic solvents.

Figure 1:
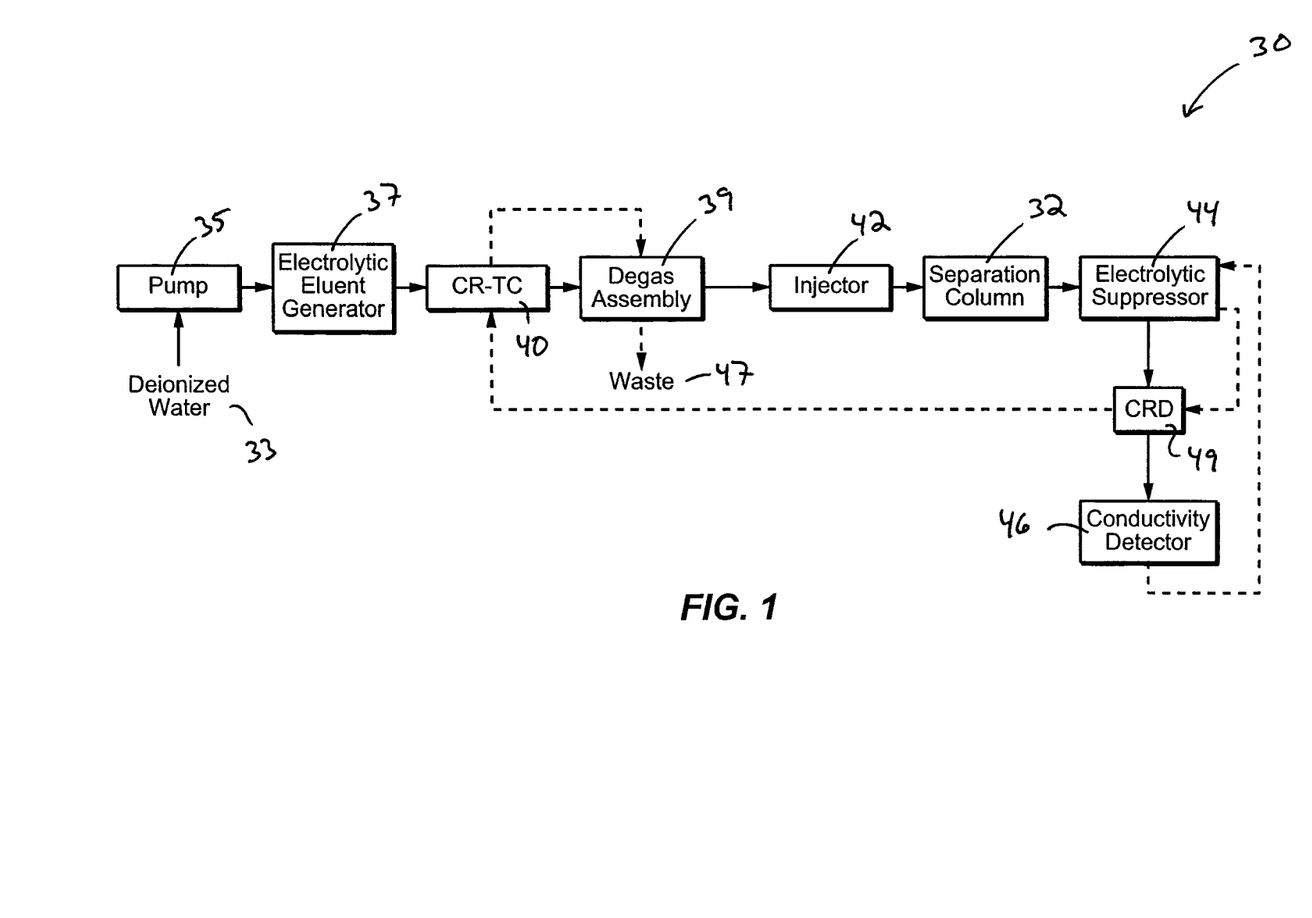
FIG. 1 is a schematic view of an exemplary high-pressure capillary degas system in accordance with various aspects of the present invention.

Turning now to the drawings, wherein like components are designated by like reference numerals throughout the various figures, attention is directed to FIG. 1, which figure represents an ion or liquid chromatography system 30 in accordance with the present invention. The system feeds a potassium hydroxide (KOH) eluent to a column 32 for analysis of a sample. A stream of deionized water from an eluent source or reservoir 33 is drawn by one or more pumps 35. The pump delivers the water stream to an eluent generator 37. An eluent purifier may also be paired with the eluent generator.

In the exemplary system, the eluent flowing from the generator includes a gas component (e.g., hydrogen) as a result of the electrolytic reaction. From the generator, the eluent flows through a degas assembly, generally designated 39, for removal of the gas. The exemplary degas assembly is provided on-line in the system and downstream from the pump, the outlet of the large capacity eluent generator, and an optional continuously-regenerated trap column (CR-TC) 40. The degassed sample is fed to a sample injector 42 for injection into the column 32, such as a separation or chromatography column. Thus, hydrogen gas is effectively removed from the KOH eluent before it reaches the sample injector of the chromatography system so that the downstream chromatographic process is not affected.

The exemplary system includes chromatographic separation means in the form of chromatographic column 32 which is packed with a chromatographic separation medium. In various embodiments, the separation medium is an ion-exchange resin. In other embodiments, the separation medium is a porous hydrophobic chromatographic resin with essentially no permanently attached ion-exchange sites. The resin system may be used for mobile phase ion chromatography (MPIC) as described in U.S. Pat. No. 4,265,634, the entire contents of which are incorporated herein for all purposes by this reference.

The eluate from column 32 is fed to a self-regenerating suppressor 44 similar to those described in U.S. Pat. No. 5,352,360 and of the type sold by Dionex Corporation of Sunnyvale, Calif. under the SRS® name. The suppressor serves to suppress the conductivity of the electrolyte of the eluent from the column but not the conductivity of the separated ions. The suppressor generally converts the electrolyte of the eluent to a weakly conducting form. The suppression process usually enhances the conductivity of the separated ions.

With continued reference to FIG. 1, the effluent from suppressor 44 is directed to a detector 46, such as a flow-through conductivity cell, for detecting the resolved ionic species. In the detector, the presence of ionic species produces an electrical signal proportional to the amount of ionic material. The output signal is typically directed from the detector to a conductivity meter thereby permitting detection of the concentration of separated ionic species.

Recycled aqueous liquid from detector 46 may be utilized as a regenerant solution. In various embodiments, the regenerant from the suppressor is used as a wash fluid to carry separated gas from degas assembly 39 to a waste receptacle 47. The regenerant solution from the detector may flow in a fluid line and serves as the solution to carry away the removed gas from the degas assembly so that the system can be operated continuously. The recycled liquid may be directed to the degas assembly directly or via other components. An optional carbonate removal device (CRD) 49 is positioned between the suppressor and detector.

Figure 2:
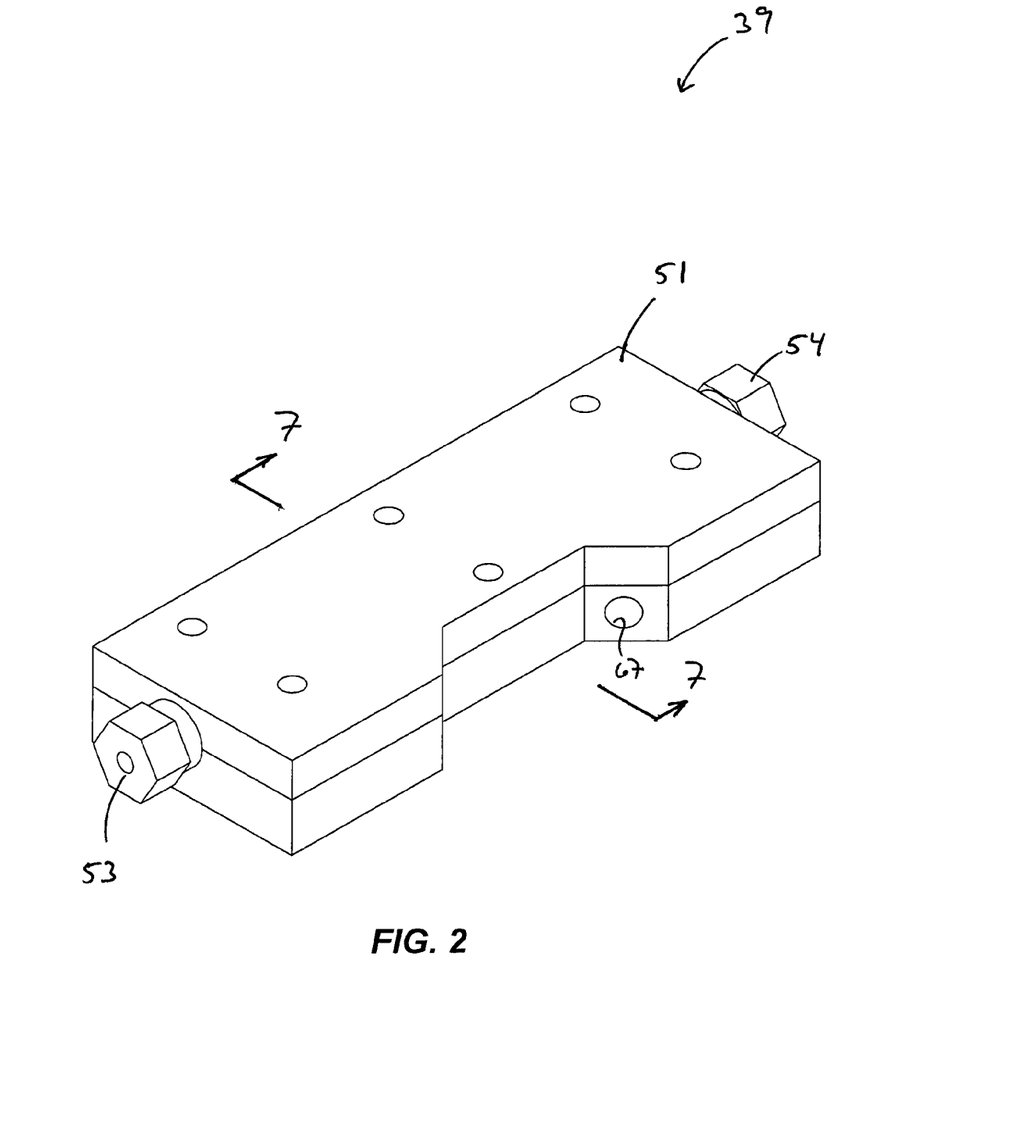
FIG. 2 is a perspective view of an exemplary gas removal assembly in accordance with various aspects of the present invention, which assembly may be used with the system of FIG. 1.
Figure 3:
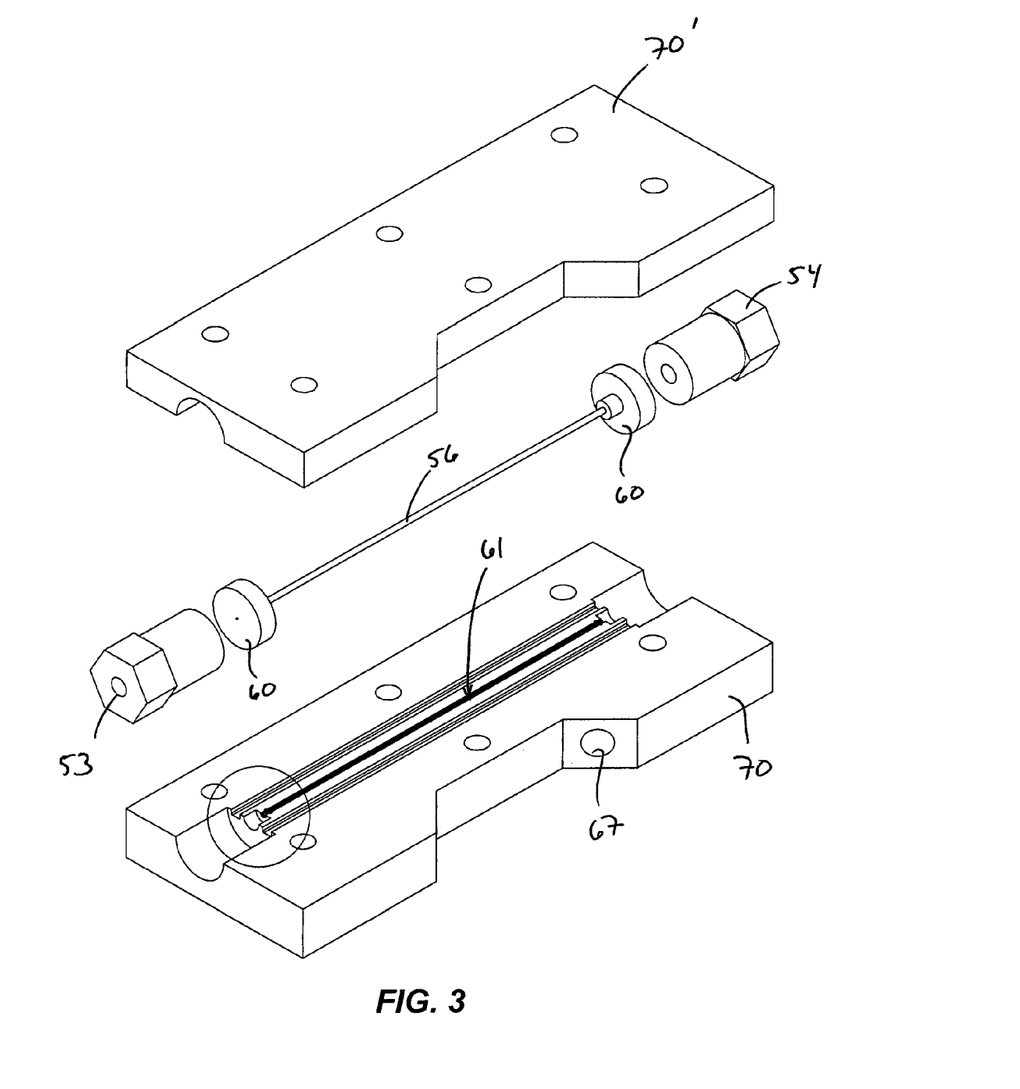
FIG. 3 is a perspective exploded view of the gas removal assembly of FIG. 2.
Figure 4:
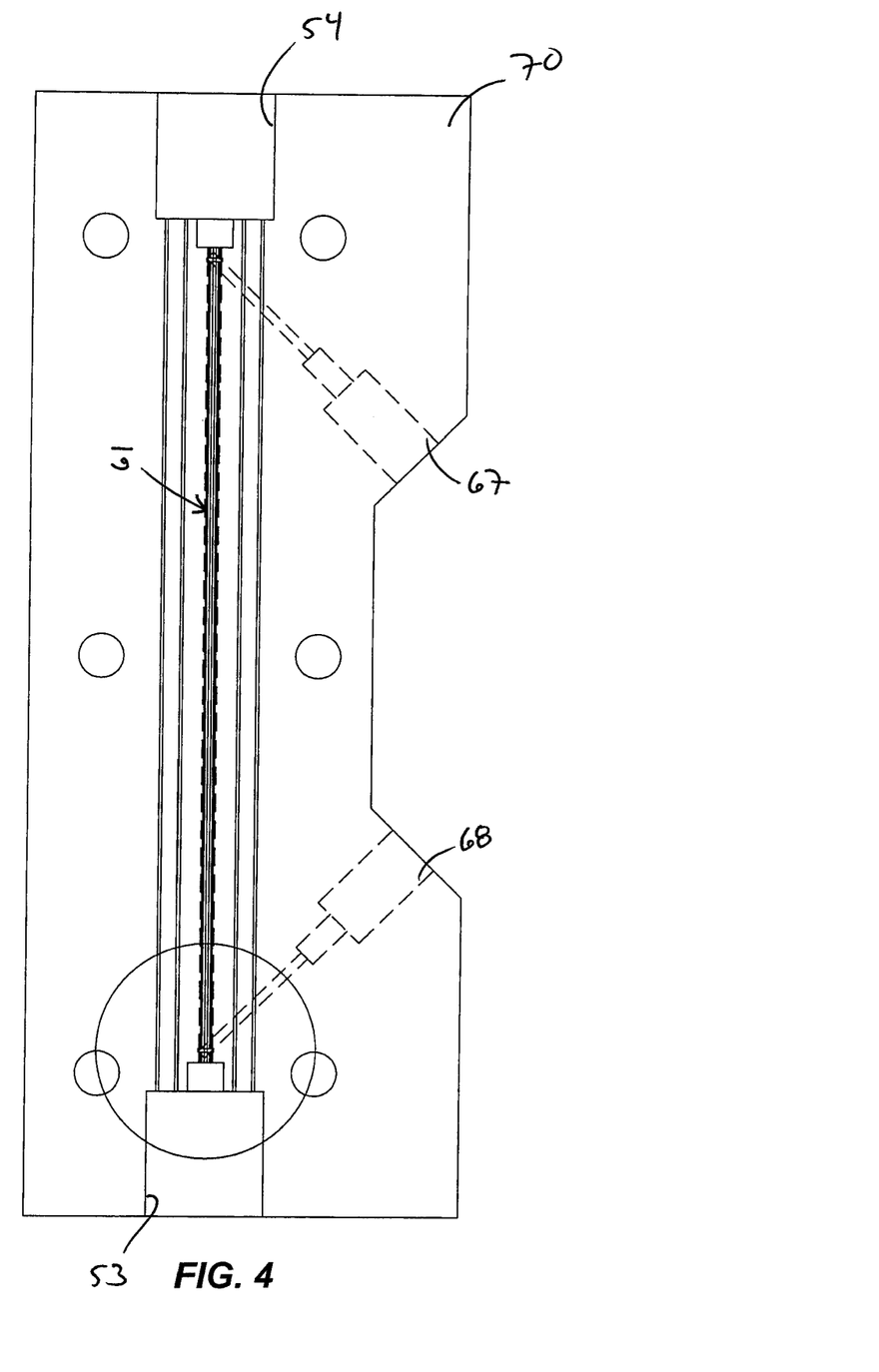
FIG. 4 is top view of a lower plate of the gas removal assembly of FIG. 2.

Turning now to FIG. 2 and FIG. 3, an exemplary degas assembly in accordance with the present invention will now be described in more detail. Various aspects of the gas removal device are similar to those described in the above-mentioned '204 patent, and to those described in the above-mentioned copending '732 application.

Generally, degas assembly 39 includes an assembly block 51 having an eluent inlet 53 and an eluent outlet 54 fluidly interconnected by a tubular degas separator 56 (see, e.g., FIG. 3). An inner diameter of the degas separator defines a pressurized fluid line 58 that extends through the assembly block from the eluent inlet to the eluent outlet. A high-pressure fluid-tight coupling between the tubular separator and respective inlet and outlet may be provided by an otherwise conventional flare seal tubing fittings 60.

Figure 10:
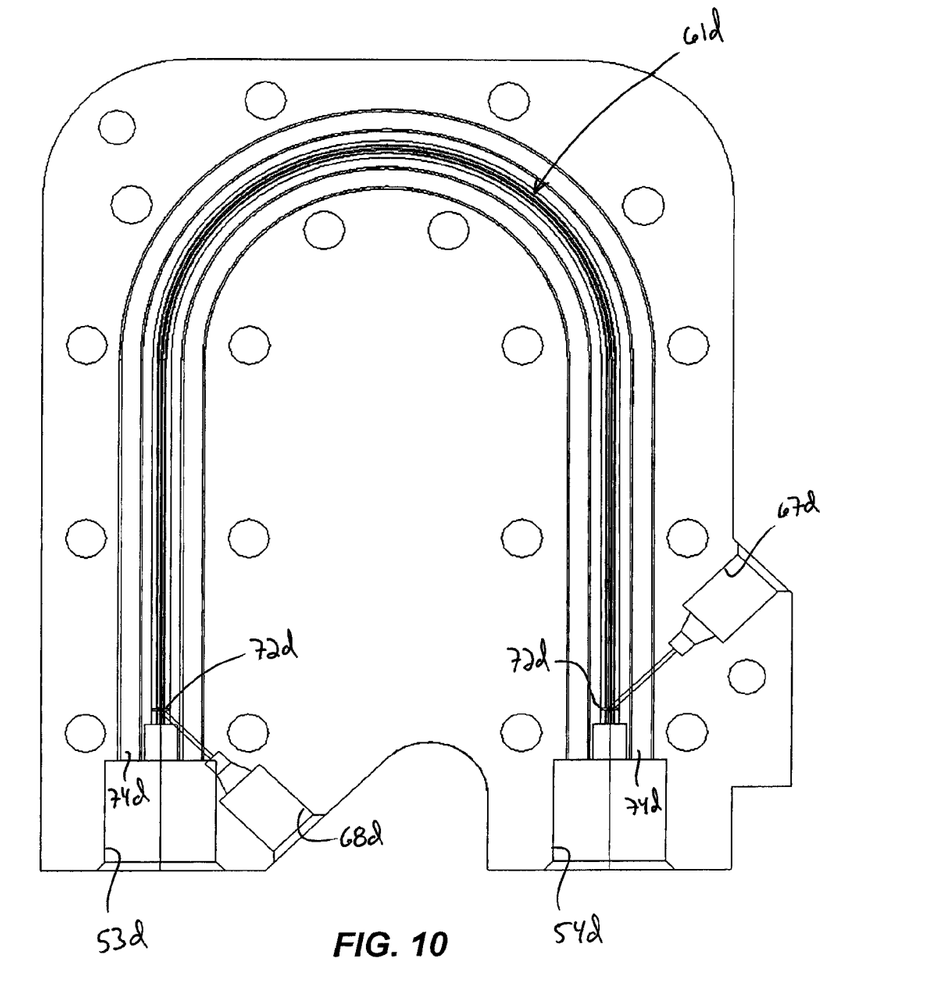
FIG. 10 is a top view another exemplary gas removal assembly in accordance with various aspects of the present invention used with the system of FIG. 1.

A separator support 61 extends within the assembly block substantially the length of degas separator 56 between the tubing fittings. In various embodiments, the degas separator and the separator support may be linear, as shown in FIG. 3. One will appreciate, however, that non-linear configurations may be utilized. For example, the degas assembly may have a U-shaped configuration as shown in FIG. 10, a serpentine or S-shaped configuration, or other suitable geometric configurations.

The separator support is dimensioned and configured to closely support an outside diameter surface of the tubular degas separator. In various embodiments, the separator support has an inner diameter that is substantially equal to the outer diameter of the degas separator. Alternatively, the inner diameter of the separator support may be less than the outer diameter of the separator thereby providing an interference fit between the separator support and degas separator.

Separator support 61 also includes a plurality of channels or grooves 63 (see, e.g., FIG. 5 and FIG. 8A) that extend the length of the support and form a low-pressure fluid line 65 for carrying a wash fluid from a wash inlet 67 to a wash outlet 68. Together with the outside diameter surface of tubular degas separator 56, the grooves define the low pressure line 65 which is a wash line maintained at a first pressure, a relatively low pressure significantly less than that of the high-pressure or pressurized line 58 carrying the eluent, or any gas-containing product.

Figures 7, 8A, 8B, 8C:
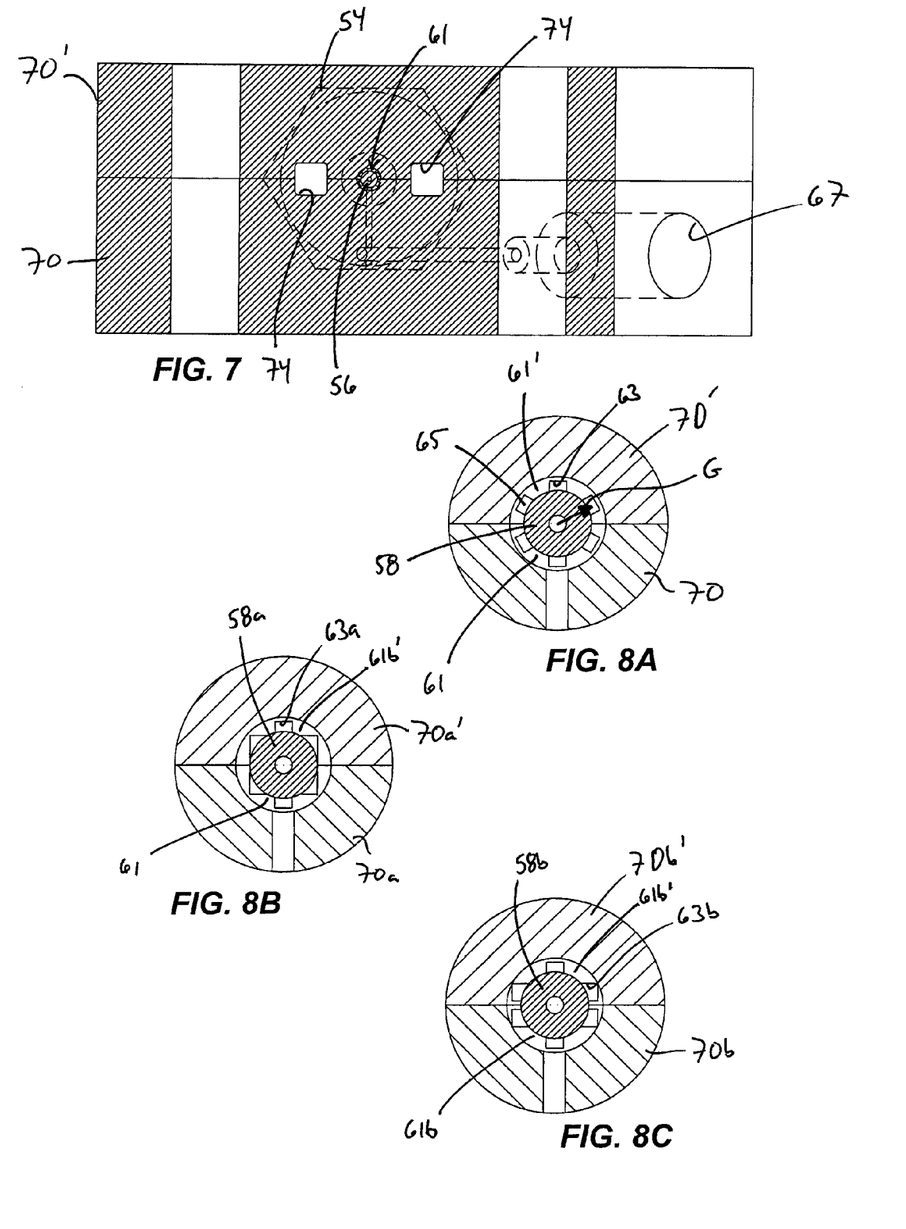

As most clearly shown in FIG. 8A, degas separator 56 defines a fluid barrier between the low-pressure and pressurized fluid lines. The separator is configured to retain liquid in the pressurized fluid line while allowing gas to flow through the separator from the pressurized line to the low-pressure line, as illustrated by arrow G. Thus, pressurized eluent flow is directed through the pressurized line 58 and the low-pressure wash that flushes to waste is in the low-pressure line 65, and eluent from eluent outlet 54 flows to column 32, as shown in FIG. 1. One will appreciate that the wash fluid and the eluent flow may flow concurrently or in opposite directions.

The exemplary degas separator is a diffusion membrane that allows gas to permeate therethrough but retains liquid on one side. In various embodiments, the degas separator blocks substantial bulk liquid flow but allows gas to permeate. In other words, the membrane functions to permit the ready transmembrane passage of gas in the product flow while substantially preventing the transmembrane passage of liquid. The gas of interest generally permeates the gas separator in a conventional manner. Preferably, the degas separator is a tubular member having a circular cross-section. One will appreciate, however, that separator may have other cross sections. For example, the inner wall of the separator may have a circular cross-section, while the outer wall may have an oval cross-section, or vise versa. Alternatively, other non-circular cross sections may also be utilized in accordance with the present invention. One will appreciate, however, that the cross-sectional shape of the separator support should be complementary in shape to the outer wall of the degas separator.

Suitable materials for the degas separator include, but are not limited to, polymers including polymethylpentene and polypropylene, and fluoropolymers such as polytetrafluoroethylene (PTFE), ethylene tetrafluoroethylene (ETFE), expanded-PTFE (ePTFE), perfluoroalkoxy (PFA), fluorinated ethylene propylene (FEP), and polyetheretherketone (PEEK). In various embodiments, the degas separator is formed of a material that is permeable by a gas under high-pressure. In various embodiments, the degas separator is a gas-permeable polymer. In various embodiments, the degas separator is an amorphous fluoropolymer tube. The exemplary degas separator is a gas-permeable tube fabricated from Teflon® AF2400 amorphous polymer sold by DuPont. One will also appreciate that the low-pressure channel member and/or degas separator may be treated with an additive or modified, such as by conjugation with a molecule. In various embodiments, the degas separator is a coating of an amorphous fluoropolymer on the exterior surface of a porous substrate tube such as Celgard®.

In various aspects of the invention, the degas separator is formed of a material selected to have one of a high gas permeability, high compressibility, low thermal conductivity, high creep resistance, and a combination thereof. The degas separator can also be used in conjunction with other features to enhance or promote separation based on ionic, chemical, and electrostatic forces. In various embodiments, the degas separator includes ion exchange sites.

The level of purity desired may depend on the application. The amount of gas separation generally depends on the diffusion properties of the gas separator, time, pressure, and diffusion area. One of skill will understand from the description herein the manner for configuring the gas separator to remove the gas and obtain the desired purity of the resulting gas-free liquid product. For example, the separation process may be configured as a multi-step process using a plurality of separation devices or by feeding product from outlet back into the degas assembly for further separation. In various embodiments, the degas assembly separates between about 50% and about 100% of the gas that enters the inlet end. In various embodiments, the degas assembly separates at least about 50% of the gas that enters the inlet end. In various embodiments, the degas assembly separates at least about 60% of the gas that enters the inlet end. In various embodiments, the degas assembly separates at least about 70% of the gas that enters the inlet end. In various embodiments, the degas assembly separates at least about 80% of the gas that enters the inlet end. In various embodiments, the degas assembly separates at least about 90% of the gas that enters the inlet end.

Turning now to FIG. 3, assembly block 51 may include a lower plate 70 and an upper plate 70' that may be secured to one another by threaded fasteners or other well known means. Suitable materials for the assembly block include polymers such as PEEK and other inert polymers, metals such as steel and stainless steel, and other suitable materials capable of providing sufficient structural integrity for supporting degas separator 56. In various embodiments, the assembly block, and the plates, are machined. One will appreciate, however, that other suitable means may be utilized to manufacture the assembly block (including the plates). For example, the plates may be molded, extruded, or otherwise shaped.

Figure 5:
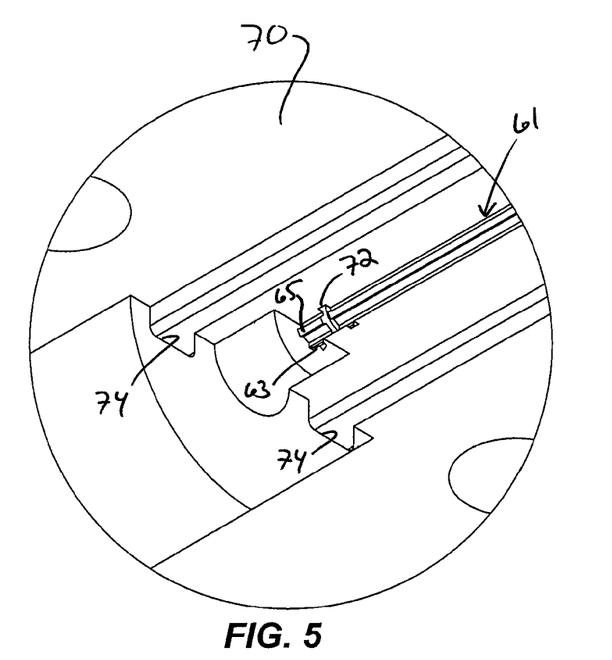
FIG. 5 is an enlarged perspective view of the lower plate of the gas removal assembly of FIG. 2 as shown in FIG. 3.
Figure 6:
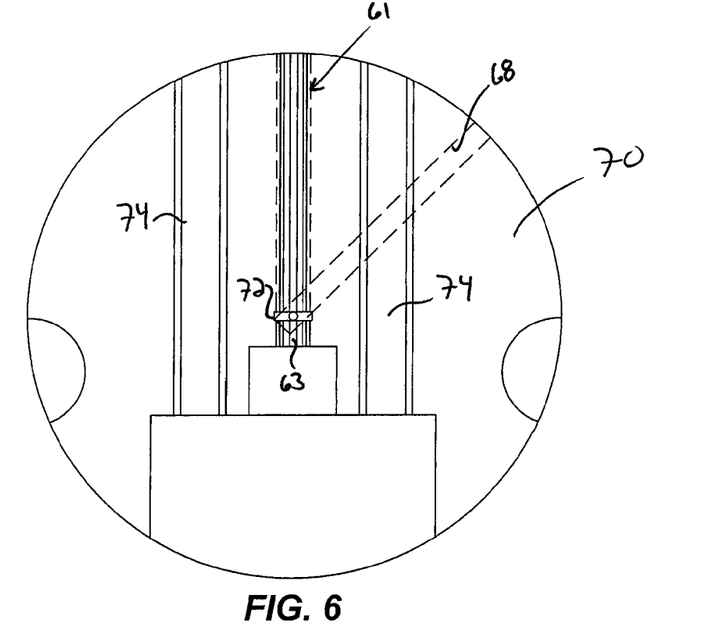
FIG. 6 is an enlarged plan view of the lower plate of the gas removal assembly of FIG. 2 as shown in FIG. 4.

The upper and lower plates having respective upper and lower separator supports 61, 61', which supports sandwich and surround degas separator 56 as the upper and lower plates are assembled together. In the illustrated embodiment, each support includes three radially extending grooves, as best seen in FIG. 5 and FIG. 8A. One will appreciate, however, that one, two, three or more grooves may be utilized to provide a suitable wash line.

Assembly block 51 may include a cut 72 that at least partially encircles degas separator 56 to fluidly couple the grooves of the lower and upper plates 70, 70', and to fluidly couple the grooves. In the illustrated embodiment, one cut couples the grooves with wash inlet 67, while another cut 72' couples the grooves with wash outlet 68. In various embodiments, the cut is an annular cut encircling the degas separator, however, one will appreciate that other geometries may also be used.

One will also appreciate that various groove configurations may be utilized in accordance with the present invention. For example, one or more or all grooves 63a may extend perpendicular to the mating surfaces of lower and upper plates 70, 70', as shown in FIG. 8B, or one or more grooves 63b may extend parallel to the mating surfaces.

Figure 9:
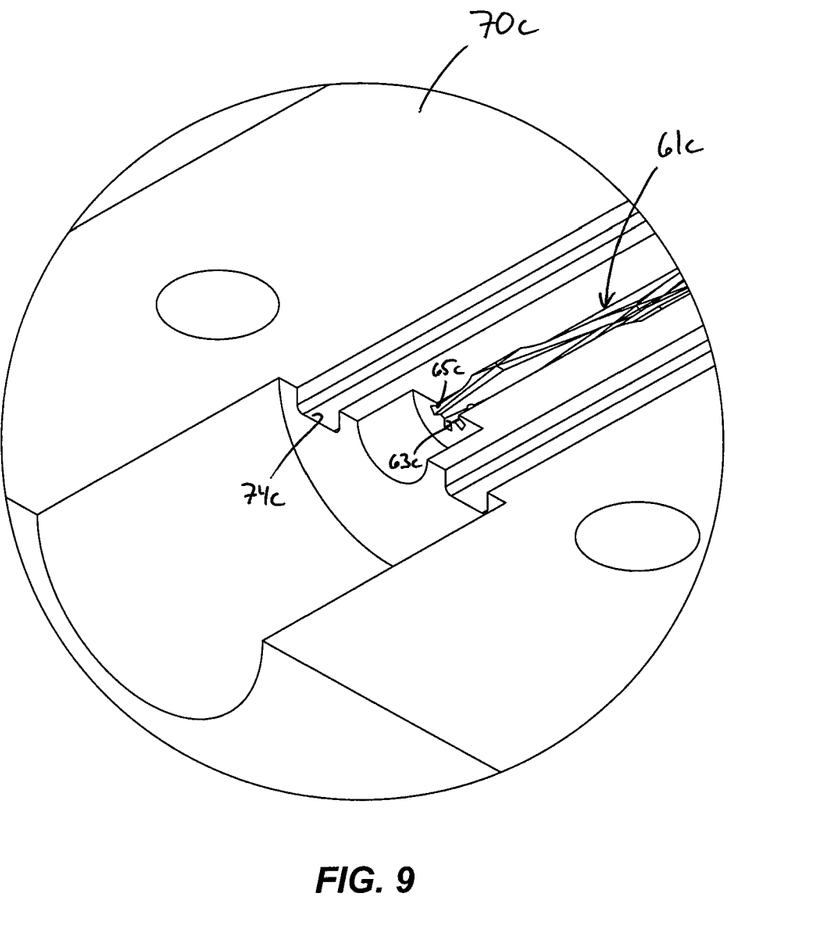
FIG. 9 is an enlarged perspective view of another exemplary lower plate of the gas removal assembly of FIG. 2 similar to that shown in FIG. 5.

In various embodiments, the grooves are linear grooves 63, as best seen in FIG. 5. However, one will appreciate that non-linear grooves may also be utilized in accordance with the present invention. For example, the grooves may helically spiral about the degas separator, as do grooves 63c in FIG. 9. In such embodiments, the helical grooves may intersect one another, thereby fluidly interconnecting the grooves. In case that the grooves are interconnected, a cut may be unnecessary to fluidly interconnect the wash inlet and outlet to all grooves, but nonetheless, a cut may be provided if so desired.

The upper and lower plates may be provided with seal channels 74 extending parallel to separator support 61. Preferably, the seal channels are dimensioned and configured to receive an elastic seal therein to prevent leakage from the wash line along the mating surfaces of lower and upper plates 70, 70'.

Returning to FIG. 3, an exemplary method of assembling the degas assembly may now be described. Each end of the tubular, gas-permeable degas separator 56 may be thermally flared. The flared ends may be compressed against the polymeric fitting components of the interfacing flare seal tubing fittings 60 housing so that the entire fluidic pathway between the fittings can be leak-free and capable of withstanding high-pressure. The separator and fittings may be then laid as a unit upon separator support 61 of lower plate 70. Next, upper plate 70' may be placed upon the lower plate, and the two secured together with threaded fasteners or other suitable means. Eluent inlet fitting 53 and eluent outlet fitting 54 may then be threaded to the assembly block in an otherwise conventional manner.

In contrast to conventional devices and methods, the makeup assembly of the present invention provides for easier and faster assembly of the gas removal device of the present invention.

It is desirable to reduce voids and dead space in fluid systems, and chromatography systems in particular. Consequently, the makeup assembly beneficially reduces dead space that would otherwise result around the inner tube.

With reference to FIG. 1 and FIG. 3, in operation, high-pressure eluent from eluent generator 37 flows to degas assembly 39 via system tubing and enters eluent inlet 53 of assembly block 51. As described above, the inlet and outlet have a low dead volume design. The inlet ports the eluent flow to pressurized line 58 within degas separator 56. Separator supports 61, 61' provide sufficient structural integrity to the outside diameter of the degas separator to allow the pressurized line therein to withstand the high-pressure of the eluent.

The eluent flow in the degas assembly is received from the eluent generator at high-pressure. In various embodiments, the pressure within the pressurized line is at least about 3300 psi, in various embodiments between about 3300 psi and about 5000 psi, in various embodiments at least about 5000 psi. The maximum pressure or peak pressure in some cases may be even higher in the pressurized line.

With continued reference to FIG. 1 and FIG. 3, the gas is removed from the gas-containing product by diffusion through the degas separator in a manner similar the degassing unit described in U.S. Pat. No. 7,390,386. The gassified eluent flows through the degas assembly where gas is separated from the liquid phase. As the gassified eluent flows through the gas-permeable tubing, gas diffuses through the member into the inner lumen and is removed by the flowing aqueous liquid stream. At the outlet end, the gas and liquid flow out of separate ports. Along the length of the pressurized channel, therefore, the amount of gas in the eluent solution decreases. In this way, the gas is separated and isolated by the degas assembly. As will be understood by one of skill in the art, the assembly can be dimensioned and configured to provide a desired amount of separation to achieve a desired sample solution purity.

The flowing aqueous liquid stream in the lumen also serves to prevent adsorption of carbon dioxide from the ambient air into the eluent stream. As described above, one source of the flowing aqueous liquid is the detector effluent. At the end of pressurized line 58, the eluent flows into outlet 54, which mirrors the inlet, and is ported to sample injector 42. After the sample has been injected into separation column 32 and thereafter detected at detector 46, the eluent (also referred to as regenerant) is directed back to the degas assembly, this time to low-pressure channel 65 where the flow sweeps away gas that has diffused through the degas separator. One will appreciate from the foregoing that the exemplary system may generally be operated continuously. In the degas assembly, high-pressure eluent may flow in the pressurized channel while recycled eluent flows through the low-pressure channel.

One will appreciate from the description herein that the gas removal assembly may have other configurations in accordance with the present invention. For example, the assembly may be non-tubular.

The degas assembly and method of the invention has several advantages. As described above, the eluent can be degassed at a higher system pressure than conventional systems using electrolytic eluent generators. In particular, conventional degas assemblies use materials such as Teflon® AF2400 tubing with a theoretical burst pressure of about 3300 psi. In practice, the system can only achieve a maximum of about 3000 psi before failure. By contrast, the system in accordance with the present inventions can operate at a pressure exceeding the maximum tensile strength of the material due to the separator support providing reinforced support structure, the system pressure can be even higher. This allows use of the degas assembly in a greater variety of systems and configurations. For example, the degas assembly may be provided in-line on the high-pressure side of the system after the pump. Conventional degas assemblies must be used off-line or in low-pressure systems.

The high-pressure capability of the degas assembly in accordance with the present invention also allows the system to be used for other applications such as RFIC-EG systems at elevated pressures. With the expanded range of system operating pressure, it is possible to increase the separation speed by performing separations at higher flow rates or using shorter separation columns packed with stationary phases of smaller particle sizes.

The annular degasser devices of the present invention can be constructed to have lower degasser volume since the degas assembly offers improved degas efficiency. To achieve the required degassing capability, degassers of lower dead volume can be prepared using the degas assembly of the present invention and the degas assembly may utilize shorter length degas tubing. The use of reduced length of the costly gas permeable tubing reduces the degasser cost. For example, Teflon AF2400 tubing currently costs about $50 per foot. The lower volume provides shorter gradient delay, improved gradient fidelity, and improved overall system performance in ion chromatography systems using electrolytic eluent generators. The degas assembly of the present invention can achieve significantly higher gradient fidelity. The improved efficiency and performance of the degas assembly in accordance with the invention also allows for use of separation columns with smaller particle sizes.

The degas assembly of the present invention makes it possible to operate an ion chromatography system using an electrolytic eluent generator at lower system operating pressures. To remove the gases from a gas-containing eluent stream using conventional degassers such as those in the Liu '129 patent, it is necessary to add some backpressure after the degasser to "squeeze out" the gases from the eluent stream. It is often necessary to maintain a backpressure threshold of about 2000 psi to achieve the desired degas efficiency. In a typical ion chromatography system using the electrolytic eluent generator, a piece of PEEK tubing with smaller ID (e.g., 0.003-inch) of appropriate length is often used to add the pressure in addition to that generated by the separation column. This approach adds to the system operation complexity. Since the degas assembly of the present invention has improved degassing efficiency, it is possible to reduce the pressure threshold to lower pressures. The need to add an additional backpressure device may be eliminated entirely. The system reliability may also be consequently improved.

The degas assembly of the invention also allows the use of a greater number and variety of lower-pressure-rating, gas-permeable tubing materials at considerable cost savings. Some of these lower tensile strength materials also offer better gas permeability. The degas assembly may also provide better rejection of contaminants coming from the suppressor such as hydrogen peroxide and ozone.

EXAMPLE

The invention is further illustrated by the following example, which is not intended to define or limit the scope of the invention.

A degas assembly 39 includes of 0.032" OD×0.008" ID AF tubing 56 which is placed inside two plates 70, 70' that have a semicircular separator support 61, 61' machined along their length, so when the plates are secured together a full circle channel is formed.

The plates are dimensioned so the AF tube OD/semicircular support interface varies from a light interference fit to a slight slip fit when plates 70, 70' are secured together. In addition small channels or grooves 63 are machined into the OD of semicircular support 61 along its length to allow regen flow past the OD of tube 56 while supporting the tube to keep stress levels below burst point failure limits.

The width and number of grooves 63 is based on the stress level on the tubing bridging the grooves and insuring the total regen-exposed circumferential OD area of tubing 56 is equal or greater than the eluent-exposed circumference of the ID area of the tubing.

A flare seal fitting 60 is provided on both ends of plate 70, 70' to seal tubing 56 against leaking from internal high-pressure eluent flow. A thin annular cut 72 is made on both plates adjacent the flare fittings and along the axis of the semicircular support on both ends of the plate. This annular cut fluidically connects all grooves 63 for regen flow.

Standard #10-32 ports are machined into plate to provide wash inlet 67 and wash outlet 68 and fluidly connected to annular cut 72 on both ends of the plate for regen flow.

The plates are designed so that, when assembled, they withstand force of 5000 psi within tubing 56 as supported by the full circle support (formed by the two assembled semicircular supports). In addition, an O-ring-type groove and seal system 74 contains the low-pressure regen flow as it travels through the small grooves 63 in plates 70, 70'.

High-pressure eluent flows to degas assembly 39 via capillary system tubing and enters inlet 53 and a corresponding flare seal fitting 60. As the eluent flows though the ID of tubing 56, the gas is removed and diffuses toward the OD of the tubing. At the opposing end of the degas assembly, an identical flare seal fitting ports the eluent flow back into capillary system tubing.

After the sample flows through detector 46, the eluent flow is directed back to degas assembly 39 where it is ported into the wash or regen flow area. The flow goes through annular cut 72, through grooves 63 cut into the circular support 61 where the degas assembly removes diffused gas. The flow goes to the other end of the plate and flows into the other annular cut 72 and out the regen out port 68.

Chromatography specifications may require the retention time RSD of detected peaks to be less than 0.2% and the plate count of the detected peak to be near its theoretical maximum. The flow geometry of the earlier designs required porting the flow from PEEK system tubing ID to AF tubing OD, and back to PEEK system tubing ID. Unfortunately, bubbles would get trapped or gradients would not get swept out cleanly going through this varying geometry, thus causing such earlier systems to fail the above specifications.

Advantageously, the degas assembly of the present invention allows for extremely high-pressure eluent to flow through in the ID of AF tubing. In accordance with the present invention, eluent flow stays in the ID of both the system tubing and the tubular degas separator, thus minimizing geometry variations that may cause flow issues noted above. Degas assemblies in accordance with the present invention provide for retention time RSD of detected peaks of less than 0.2%.

For convenience in explanation and accurate definition in the appended claims, the terms "upper" and "lower", etc. are used to describe features of the exemplary embodiments with reference to the positions of such features as displayed in the figures.

In many respects various modified features of the various figures resemble those of preceding features and the same reference numerals followed by subscripts "a", "b" and "c" designate corresponding parts.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A high-pressure capillary degas assembly comprising:
an assembly block including an eluent inlet and an eluent outlet, and a separator support extending therebetween, the assembly block also including a wash inlet and a wash outlet and a groove extending therebetween;
a tubular separator extending within the assembly block, the separator including an inner surface and an outer surface, the inner surface defining an eluent fluid line fluidly interconnecting the eluent inlet and outlet, the outer surface abutting against the separator support and enclosing the groove to define a wash line within the groove;
wherein the separator is configured to retain liquid in the eluent fluid line at a first pressure and allow gas to flow through the separator to the wash fluid line at a second pressure lower than the first pressure.

2. The degas assembly according to claim 1, wherein the assembly block comprises a plurality of grooves extending between the wash inlet and the wash outlet, wherein outer surface of the separator encloses each of the plurality of grooves.

3. The degas assembly according to claim 2, wherein the plurality of grooves extend radially away from the separator.

4. The degas assembly according to claim 2, wherein the plurality of grooves extend along substantially the entire length of the separator.

5. The degas assembly according to claim 2, wherein the plurality of grooves collectively form the wash line which extends coaxially around the eluent line.

6. The degas assembly according to claim 2, wherein the assembly block comprises a cut at least partially encircling the tubular separator fluidly coupled with one of the wash inlet and wash outlet, the annular cut interconnecting the plurality of grooves.

7. The degas assembly according to claim 6, wherein the cut is an annular cut encircling the tubular separator.

8. The degas assembly according to claim 2, wherein one or more of plurality of grooves helically spiral about the tubular separator.

9. The degas assembly according to claim 8, wherein two or more of the plurality of grooves intersect one another fluidly coupling the two or more grooves with one another.

10. The degas assembly according to claim 2, wherein the assembly block comprises upper and lower plates, and respective upper and lower supports on the upper and lower plates.

11. The degas assembly according to claim 10, wherein the upper and lower plates have corresponding seal channels extending parallel to the separator support, the corresponding seal channels receiving a seal therein to fluidly seal the wash line.

12. The degas assembly according to claim 10, wherein the upper and lower plates have corresponding mating surfaces, wherein at least one of said plurality of grooves extends away from the separator and parallel to the mating surfaces.

13. The degas assembly according to claim 10, wherein the upper and lower supports have an inner diameter that is substantially equal to an outer diameter the outer surface of the separator.

14. The degas assembly according to claim 13, wherein the inner diameter of the upper and lower supports is less than the outer diameter of the separator thereby providing an interference fit between the separator and separator support.

15. The degas assembly according to claim 1, wherein the tubular separator has a circular cross-section.

16. The degas assembly according to claim 1, wherein the tubular separator comprises inert polymer tubing.

17. The degas assembly according to claim 16, wherein the polymer tubing is amorphous fluoropolymer tubing.

18. The degas assembly according to claim 16, wherein the polymer tubing is polyetheretherketone (PEEK) tubing.

19. The degas assembly according to claim 1, wherein the eluent line receives eluent from an eluent generator at a pressure up to at least approximately 3000 psi.

20. The degas assembly according to claim 19, wherein the eluent line receives eluent from an eluent generator at a pressure up to at least approximately 5000 psi.

21. A liquid chromatography system comprising:

the degas assembly according to claim 1; and a pressurized liquid chromatography column;

wherein eluent flows from the eluent outlet of the assembly block to the chromatography column.

* * * * *